(12) United States Patent
Carvalho

(10) Patent No.: US 6,500,159 B1
(45) Date of Patent: Dec. 31, 2002

(54) CORRUGATED SANITARY NAPKIN

(75) Inventor: Antonio Carlos Ribeiro Carvalho, SP (BR)

(73) Assignee: Johnson & Johnson Industria e Comercio LTDA I 3170 (BR)

( * ) Notice: Subject to any disclaimer, the term of this patent is extended or adjusted under 35 U.S.C. 154(b) by 26 days.

(21) Appl. No.: 09/713,465

(22) Filed: Nov. 15, 2000

(51) Int. Cl.[7] ................................................. A61F 13/15
(52) U.S. Cl. .................................. 604/385.01; 604/358
(58) Field of Search ........................ 604/385.02, 385.01, 604/385.04, 385.16, 317–402; 2/400–406, 267, 268

(56) References Cited

U.S. PATENT DOCUMENTS 3,653,382 A * 4/1972 Easley et al. ............... 128/284
4,389,211 A * 6/1983 Lenaghan ................... 604/383
5,591,150 A    1/1997 Olsen et al.
5,993,431 A * 11/1999 Mcfall et al. ............ 604/385.2

FOREIGN PATENT DOCUMENTS

EP    0 137 644 A2    4/1985
EP    0 888 765 A1    1/1999

* cited by examiner

*Primary Examiner*—Jeanette Chapman

(57) ABSTRACT

The present invention is related to a women's disposable sanitary napkin for external use. More specifically, a women's disposable sanitary napkin is provided with corrugations conformable in its whole structure, which makes it possible to adapt the sanitary napkin to the wearer's undergarment.

7 Claims, 2 Drawing Sheets

CORRUGATED SANITARY NAPKIN

FIELD OF THE INVENTION

The present invention relates to a women's disposable sanitary napkin for external use and more specifically to a women's disposable sanitary napkin that is provided with conformable corrugations in its whole structure, which makes it possible to adapt the sanitary napkin to the wearer's undergarment according to her needs.

BACKGROUND OF THE INVENTION

Women's disposable sanitary napkins are articles widely known in the state of the art that comprise an absorbent core sandwiched between two layers known as top sheet and lining sheet. The top sheet is permeable to fluids and its function is to allow the passage of the menstrual fluid towards the absorbent core, thus keeping the fluid away from the wearer's body. It can be comprised of a layer of a material other than a fabric or composed of a perforated plastic film for performing the function.

The lining sheet is generally impermeable to or resistant to the passage of liquids and is used to prevent the fluid absorbed by the absorbent core from leaking. It may comprise a non-perforated plastic sheet or any other material having such features.

The absorbent core is composed absorbent fibers and/or particles such as synthetic cellulosic or textile fibers such as rayon, polyester and the like. Its purpose is to contain the vaginal exudates. The absorbent core may optionally contain a superabsorbent material having a varying range of particle sizes and be may distributed either uniformly throughout the core or alternatively in discrete regions of the core, for example, as a layer, as a film, or as individual particles. One example of a conventional superabsorbent material that can be used is sodium polymethacrylate.

The conventional features in a woman's disposable sanitary napkin include a shape that adapts to the woman's anatomy, it should be capable of quickly absorbing liquids, it is preferably releasably affixed to the undergarment during use, and it is preferably discreet and comfortable.

The conventional women's disposable sanitary napkin deforms from its initial configuration due to the wearer's movement changes, for the movement tends to conform the napkin to the geometry of the space between the wearer's thighs This deformation has been found to cause discomfort to the wearer and may also result in premature leakage.

Previous attempts to overcome these problems have tried to optimize the efficiency of those disposable products by using static concepts of the body shape in the pulp and improving the absorption of the menstrual fluid. Examples of articles of the state of the article the purpose of which is the anatomical adaptation include the hourglass shape used in women's sanitary napkins, for example in U.S. Pat. No. 3,805,790 (Kimberly-Clark) and U.S. Pat. No. 4,758,241 (Elissa D. Papajohn). The configuration takes into account the space between the wearer's thighs close to the vaginal region, thus providing an improvement over rectangular-shaped articles, but the women's napkins did not take into account the individuality of the space between the wearer's thighs and the variety of undergarment used nowadays.

Another example of a women's sanitary napkin has a corrugated absorbent core, for example in U.S. Pat. No. 3,411,504 (J. A. Glasman). The women's sanitary napkin in this patent includes an absorbent core provided with longitudinal embossed lines for a faster flow of the menstrual fluid. However, the napkin design in this patent did not take into account the wearer's anatomy.

Still another example of a women's sanitary napkin is disclosed in U.S. Pat. No. 3,954,107 (Colgate Palmolive). This sanitary napkin is provided with two parallel longitudinal absorbent cores having a channel therebetween whose function is to collect the fluid and direct same to the longitudinal ends of the article, not aiming at the women anatomy or comfort.

SUMMARY OF THE INVENTION

Figure 1:
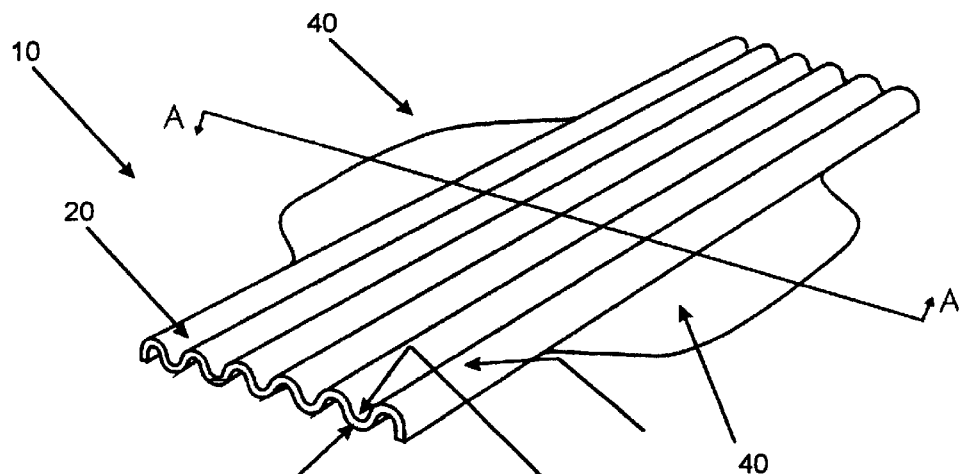
FIG. 1—a perspective view of the women's sanitary napkin in accordance with the present invention.

It is an object of the present invention to overcome the above described inconveniences by providing an improved sanitary napkin that is capable of adapting to a wearer's anatomy and has an efficient absorption system.

In accordance with the present invention, there has been provided a women's disposable sanitary napkin for external use characterized by having longitudinal corrugations formed in its whole structure that allows the sanitary napkin to laterally extend and/or contract and thus adapt to a wearer's undergarment according to her individual needs.

DETAILED DESCRIPTION OF THE PREFERRED EMBODIMENTS

The sanitary napkin of the present invention has a structure wherein a plurality of corrugations extend longitudinally throughout the sanitary napkin and provides a corrugated structure that is adaptable according to the wearer's needs at the time she puts the sanitary napkin on. The corrugations are disposed in such a way that they are parallel to the longitudinal axis of the product before use. The corrugations may be regularly spaced across the width of the article or alternatively may be randomly spaced.

The sanitary napkins having corrugations of the present invention are conformable and are preferably expandable or extensible to adapt to all and any extension or side compression against the sanitary napkin, in a way that the sanitary napkin can be extended and positioned by the wearer in the required place when she puts it on. The extensibility of the sanitary napkin attained by the corrugations provides a better adequacy to the dimensions of the undergarment, thus providing comfort and safety to the wearer.

In accordance with a preferred embodiment, the present invention relates to a conformable corrugated women's sanitary napkin wherein the sanitary napkin is provided with a plurality of longitudinal folds that are formed in such a way that the corrugations are maintained in a corrugated form at least until the moment of use and are capable of being stretched to laterally expand the width of the sanitary napkin. In accordance with this embodiment, the corrugation of the corrugated structure of the sanitary napkin may be maintained by stabilizing means along one of the sides of the corrugation. That is, each corrugation has an upper surface and a lower surface and includes a cavity portion and an adjacent protuberance portion, each cavity portion sharing a wall with an adjacent protuberance portion. The stabilizing means is preferably located on a lower surface of a longitudinally extending cavity along one of its walls.

The corrugations must be kept at least until the time the napkin is put on, in such a way that the structure of the sanitary napkin can be adapted to the wearer's needs, that is, the conformable corrugations must provide a lateral extensibility to the structure of the sanitary napkin whenever required. The choice of a particular corrugation process may vary widely, depending on the type of materials used to form the absorbent structure. The corrugation can be attained, for example, through heating, adhesive application, embossing of the tips by means of heat, adhesive, or both, and the like. In the event of corrugation through the application of an adhesive, a suitable adhesive is the pressure sensitive adhesive (PSA).

A suitable way to maintain the structure of the sanitary napkin is to spray an adhesive on a smooth surface, for example a film, and then overlap the structure of the previously corrugated sanitary napkin over the film. At the time it is put on, the smooth surface is removed, the ends are extended and/or compressed and then attached to the undergarment.

Another typical way to conform the structure of the sanitary napkin is to apply adhesive lines in the inner regions of the protuberances of the corrugations and to place the corrugations close to one another. At the time it is put on, the ends of the sanitary napkin are extended and/or compressed, thus exposing the adhesive regions for attaching the napkin to the wearer's undergarment.

The corrugation or longitudinal fold of the absorbent structure is attained by procedures known to one skilled in the art, for example, the use of a male-female configuration.

The sanitary napkin of the present invention may also comprise side fastening wings.

The present invention will be described below through the accompanying drawings that represent a preferred embodiment, without excluding other alternative embodiments of protection defined in the attached claims. Referring now to FIG. 1, the women's sanitary napkin 10 of the present invention is comprised of a substantially oblong absorbent core 25 disposed between two layers known as top sheet 20 and lining sheet 30.

The top sheet 20 is permeable to fluid and its function is to allow the passage of the menstrual fluid towards the absorbent core 25, thus keeping the fluid away from the wearer's body. Therefore, it should comprise a layer of a material other than fabric or made of a perforated plastic film or any material that performs this function.

The lining sheet 30, opposite the top sheet 20, is impermeable or resistant to the passage of liquids and used to prevent the fluid absorbed by the absorbent core 25 from leaking. Therefore, it should comprise a non-perforated plastic sheet or any other material having such features.

Still according to the present invention, the women's sanitary napkin 10 is preferably provided with wings or borders 40 that if extend laterally from the top sheet 20 and/or of the lining sheet 30 of the women's sanitary napkin 10. The wings are adapted to be folded over a crotch portion of a wearer's undergarment in use and help in the attachment of the napkin to the wearer's undergarment. In the lower part of each side wing, there is an adhesive 60 covered by a removable protection sheet 50.

Figure 2:
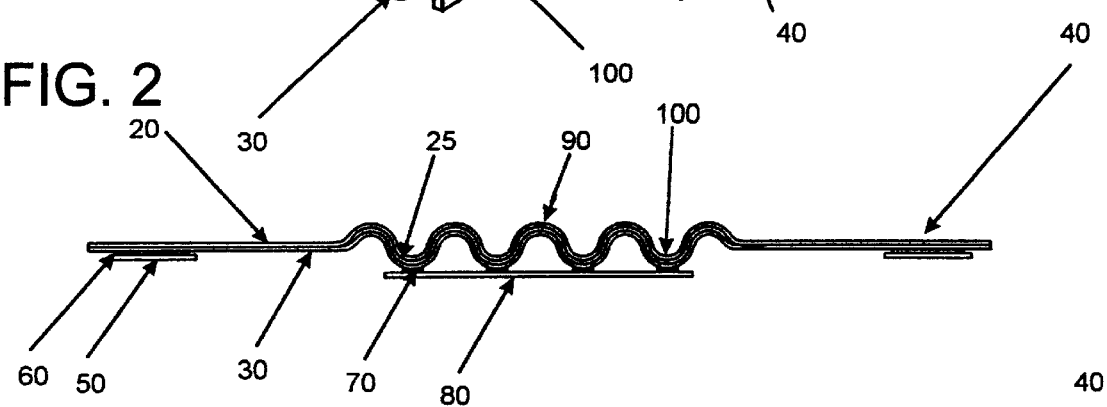
FIG. 2—a cross-sectional cut view cut of the women's sanitary napkin illustrated in FIG. 1.

As shown in FIG. 2, the women's sanitary napkin 10 is provided with longitudinal conformable corrugations that can extend throughout its whole structure. Such corrugations are formed by alternating protuberances 90 and cavities 100. The protuberances 90 and cavities 100 are not necessarily regular.

The corrugated structure of the women's sanitary napkin 10 can be maintained until the time of use by the adhesive regions 70 located in the lower part of the cavities 100, protected by a removable protection sheet 80.

Figure 3:
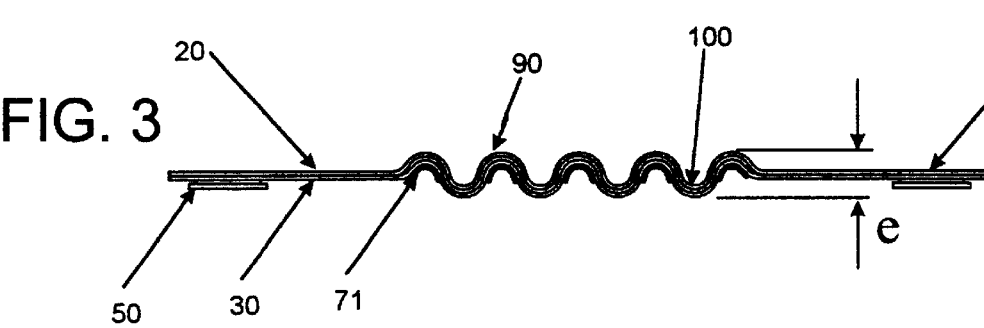
FIG. 3—a cross-sectional cut view of a variation of the corrugation of the women's sanitary napkin illustrated in FIG. 1.
Figure 4:
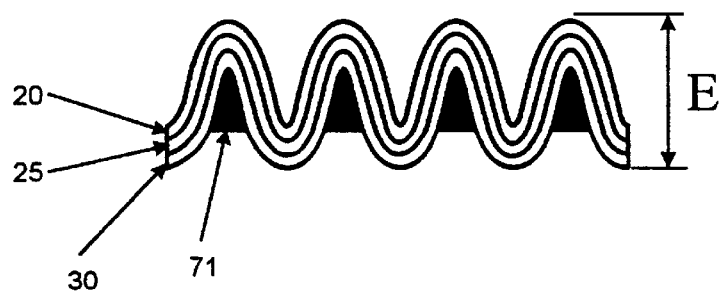
FIG. 4—a detailed cross-section cut view cut of the variation of the corrugation illustrated in FIG. 3, with the corrugations close to one another.

FIG. 3 shows another alternative of the stabilization of the corrugated structure of the women's sanitary napkin 10, wherein the structure is maintained through the application of adhesive 71 to the lower part of the protuberances 90, and the corrugations are disposed close to one another as shown in FIG. 4. In FIG. 3, it is also shown an apparent thickness "e" characterized by the formation of the corrugations. The same happens in FIG. 4, wherein the apparent thickness "E" is formed by the approximation of the corrugations. Preferable, "E" up to fifteen times higher than "e".

Figure 5:
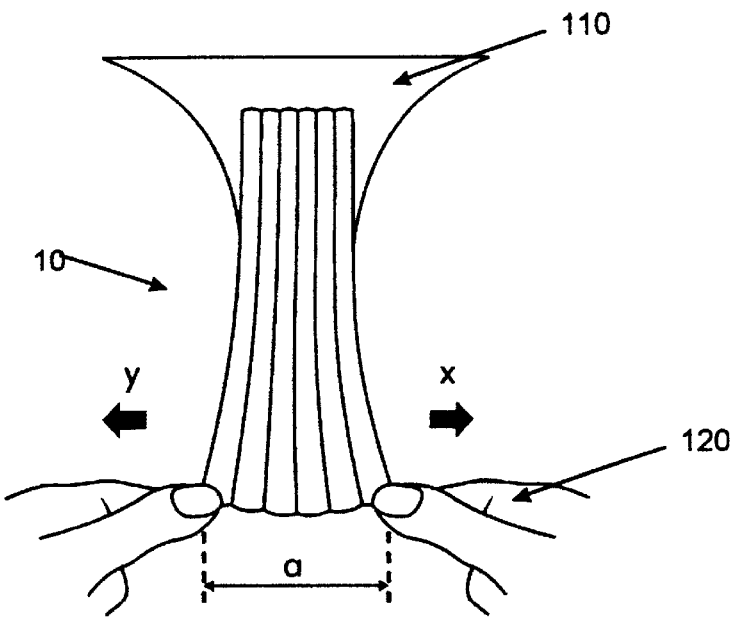
FIG. 5—a view of the women's sanitary napkin of the invention, when it is initially adjusted to the undergarment.

FIG. 5 shows the women's sanitary napkin 10 at the time it is placed on the undergarment 110 of the wearer 120. The napkin can be extended in the front portion in direction X as far as a position "a" according to the needs of the wearer 120.

Figure 6:
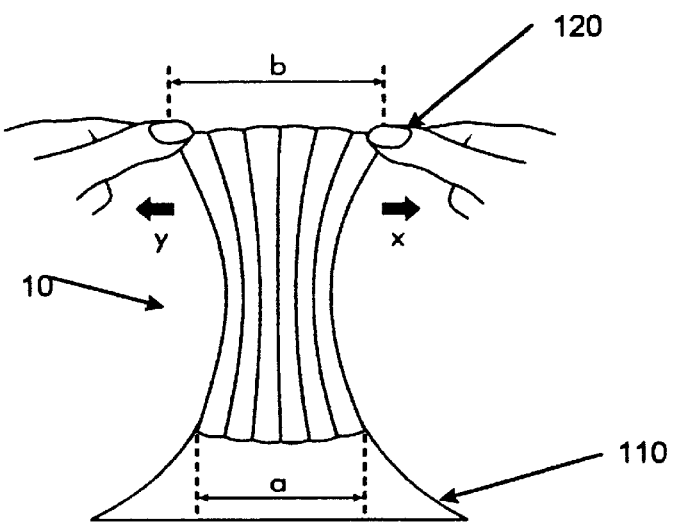
FIG. 6—a view of the women's sanitary napkin of the invention, in the sequence of the adjustment to the undergarment.

Similarly, in FIG. 6 the women's sanitary napkin 10 is shown extended in the lower part, in direction X as far as a position "b" according to the needs of the wearer 120.

Preferably, the positions "a" and "b" can be extended as far as about five times the initial width of the corrugated absorbent.

Figure 7:
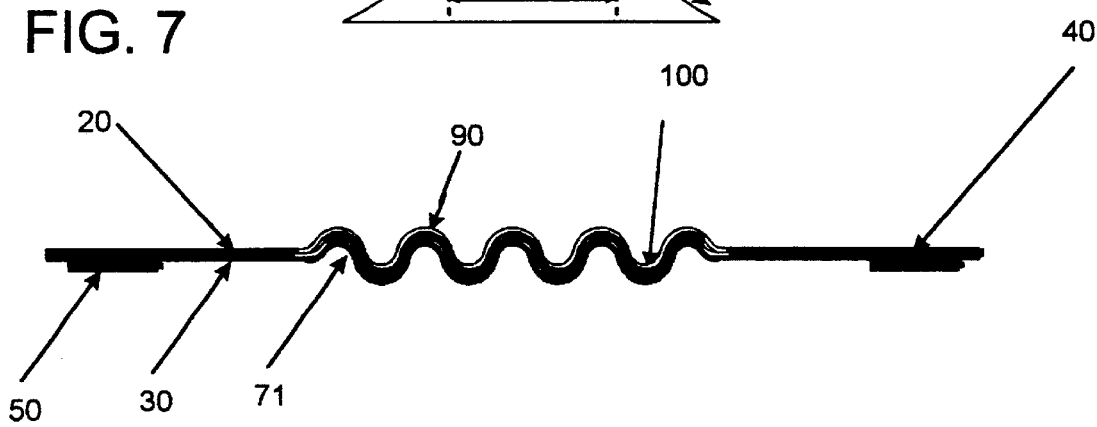
FIG. 7—a cross-section cut view of the women's sanitary napkin illustrated in FIG. 1.

FIG. 7 shows another alternative of the stabilization of the corrugated structure of the sanitary napkin 10, wherein the structure is maintained through the application of adhesive 71 to the lower part of the protuberances 90 and cavities 100 continuously.

What is claimed is:

1. A disposable women's sanitary napkin having a length and a width and comprising an absorbent core disposed between a top sheet and a lining sheet, the napkin further including a plurality of longitudinally extending corrugations that extend along the entire length and thickness of the sanitary napkin, the corrugations being adapted to allow the sanitary napkin to extend and/or contract to a wearer's undergarment in use.

2. A disposable women's sanitary napkin according to claim 1, wherein the sanitary napkin has an initial width when the corrugations are in an unstressed condition and an extended width when a laterally extending force is applied to the napkin and wherein the extended width is up to about five times the initial width of the sanitary napkin.

3. A disposable women's sanitary napkin according to claim 1, wherein the absorbent core, top sheet and lining sheet have a combined thickness, the napkin has an apparent thickness of up to about five times the combined thickness of the absorbent core, top sheet and lining sheet.

4. A disposable women's sanitary napkin according to claim 1, wherein the sanitary napkin has a pair of opposite longitudinally extending sides and a flexible wing extending laterally outward from each longitudinally extending side in a central region of the napkin.

5. A disposable women's sanitary napkin according to claim 1, wherein each corrugation includes at least one cavity and at least one protuberance, the cavity having an adhesive region and wherein a smooth surface contacts the adhesive region on the cavity.

6. A disposable women's sanitary napkin according to claim 1, wherein each corrugation includes at least one cavity and at least one protuberance, the protuberance having an adhesive line extending along a substantial portion of the corrugation.

7. A disposable women's sanitary napkin according to claim 6, wherein the adhesive lines disposed between the protuberances and cavities.

* * * * *